United States Patent
Monroe

(10) Patent No.: US 11,154,474 B2
(45) Date of Patent: Oct. 26, 2021

(54) CHEMICAL FORMULATIONS AND THEIR USE IN NEUTRALIZING OR ELIMINATING ODORS

(71) Applicant: Manus B. Monroe, Sebastopol, CA (US)

(72) Inventor: Manus B. Monroe, Sebastopol, CA (US)

(*) Notice: Subject to any disclaimer, the term of this patent is extended or adjusted under 35 U.S.C. 154(b) by 34 days.

(21) Appl. No.: 16/280,112

(22) Filed: Feb. 20, 2019

(65) Prior Publication Data

US 2019/0209450 A1 Jul. 11, 2019

Related U.S. Application Data

(63) Continuation of application No. 14/758,399, filed as application No. PCT/US2013/029787 on Mar. 8, 2013, now abandoned.

(51) Int. Cl.

| | |
|---|---|
| *A61K 8/365* | (2006.01) |
| *A61L 2/18* | (2006.01) |
| *A61L 9/14* | (2006.01) |
| *A61L 9/014* | (2006.01) |
| *A61K 8/02* | (2006.01) |
| *A61Q 15/00* | (2006.01) |
| *A61K 8/26* | (2006.01) |
| *A61L 9/01* | (2006.01) |

(52) U.S. Cl.
CPC ............ *A61K 8/365* (2013.01); *A61K 8/0283* (2013.01); *A61K 8/26* (2013.01); *A61L 2/18* (2013.01); *A61L 9/01* (2013.01); *A61L 9/014* (2013.01); *A61L 9/14* (2013.01); *A61Q 15/00* (2013.01)

(58) Field of Classification Search
CPC .................................................. A61K 8/0283
See application file for complete search history.

(56) References Cited

U.S. PATENT DOCUMENTS

| | | | |
|---|---|---|---|
| 3,317,372 A | 5/1967 | Hart et al. | |
| 4,325,939 A | 4/1982 | Shah et al. | |
| 4,902,434 A | 2/1990 | Dickerson et al. | |
| 5,076,960 A | 12/1991 | Hutchings et al. | |
| 6,200,939 B1 * | 3/2001 | Maurer | C11D 1/66 134/42 |
| 2006/0051430 A1 | 3/2006 | Arata et al. | |
| 2006/0251597 A1 | 11/2006 | Yu et al. | |
| 2008/0145267 A1 * | 6/2008 | Do | A61K 8/0208 422/5 |
| 2009/0092571 A1 | 4/2009 | Hirano et al. | |
| 2009/0170932 A1 * | 7/2009 | Aggarwal | A01N 41/12 514/474 |
| 2010/0158840 A1 * | 6/2010 | Hiramoto | A61K 8/19 424/65 |

FOREIGN PATENT DOCUMENTS

WO 2013013902 A2 1/2013

* cited by examiner

*Primary Examiner* — Sarah Alawadi
(74) *Attorney, Agent, or Firm* — Patent Success Strategies, LLC; David B. Waller

(57) ABSTRACT

The present invention is a chemical formulation and method of using the chemical formulation to neutralize or eliminate odors on a surface. In one aspect, the chemical formulation is an aqueous solution of multi-valent citrate salts and a surfactant that may further comprise a fragrance and/or a color and/or a chelating agent. The method comprises the steps of applying this formulation in sufficient volume to saturate the surface thereby neutralizing or eliminating the odor. In another aspect, the formulation of multi-valent citrate salts may be applied in solid form to an odorous aqueous solution or may be used to coat an absorbent matrix that is expected to receive an odorous aqueous solution.

5 Claims, No Drawings

CHEMICAL FORMULATIONS AND THEIR USE IN NEUTRALIZING OR ELIMINATING ODORS

CROSS-REFERENCE TO RELATED APPLICATIONS

This patent application is a continuation-in-part application of patent application Ser. No. 14/758,399 filed 29 Jun. 2015 and claims the benefit of the filing date of PCT/US2013/29787 filed 8 Mar. 2013 under 35 U.S.C. § 371.

STATEMENT REGARDING FEDERALLY SPONSORED RESEARCH OR DEVELOPMENT

None

INCORPORATION-BY-REFERENCE OF MATERIAL SUBMITTED ON COMPACT DISC

None

BACKGROUND OF THE INVENTION

(1) Field of the Invention

The present invention relates to chemical formulations and their use in neutralizing or eliminating odors. Specifically, odors associated with decomposition, excrement, biological excretions, microorganisms or the burning of plant material.

(2) Description of Related Art

Unpleasant odors can result from a variety of natural sources including burning material, decomposing plant or animal material, animal excrement or excretions and microorganisms. Historically, these odors often warned of potential dangers. The smell of smoke usually indicated fire. The smell of rotting meat could have meant the presence of predators. Water having an unusual smell generally meant avoid drinking. However, these concerns have diminished over time and today individuals are more concerned with eliminating these odors than the warnings they provided in the past.

The effect of many unpleasant odors range in severity from being a nuisance to causing serious medical conditions in certain individuals. Consequently, there are a large variety of commercially available formulations for managing odors. These formulations attack odors through a number of chemical processes that can cause health concerns and do not often eliminate the odor. For example, one common process or method is to introduce a fragrance that masks the unpleasant odor. However, this can become a health problem for an individual susceptible to that odor if they are not able to recognize it and leave the area. Other methods use chemicals that are relatively safe in low concentrations but become a health risk as concentrations rise from continued use or increased exposure. It is also common to use agents that kill odor-producing microorganisms. However, if these agents are inhaled they can damage the symbiotic microorganisms necessary for proper health. Therefore, understanding the sensory system of smell and how certain chemical compounds are able to produce the sensation of odor is important for developing formulations to safely mitigate their effect.

The ability to smell, known as olfaction, is a complex process involving various parts of the brain and the mucous membranes lining the walls of the nasal cavity. The mucous membranes, or olfactory epithelium, are composed of olfactory neurons containing cellular receptors. The number and type of receptors present will vary depending on the individual. Detection occurs when the odorous compounds dissolve in the mucous membrane and bind the cellular receptors. A variety of different receptors interact with each odorous compound. Their binding creates a neural impulse response comprising a unique signal pattern that is transmitted to the olfactory bulb, which is then relayed to the neocortex and hypothalamus. The neocortex deciphers these signal patterns allowing humans to discriminate and perceive up to ten thousand different odors.

The hypothalamus activates smell-related emotions and the olfactory relationships with memory and survival. These emotions regulate heart rate, blood pressure, respiration and digestive activity. The extent of the physical and mental affect depends on the chemical compounds and the individual's memory association of that odor.

The ability of smell to affect the physical, mental and emotional state of an individual is generally proportional to the intensity of the odor and the frequency of exposure. This is because these chemicals enter the blood stream through the mucous membranes of the respiratory tract, as well as the fluid surrounding the eyes and the surface of the skin. Consequently, increased concentration or exposure to unpleasant odors can trigger unwanted reactions such as headache and irritation to the nose, eyes and throat. In more serious reactions, asthma, hypersensitivity and anaphylactic shock can result. The extent of this reaction varies with each individual and is dependent on their past exposure, physical condition and the frequency, concentration, and duration of an odor.

For a compound to be odorous it must be capable of entering a gaseous state and contain a chemical group that can be detected by olfaction. There are a number of chemical groups that are known to produce odorous compounds. These include volatile organic compounds such as organic acids, aldehydes, ketones, amines, sulfides, thiols, indoles and phenols. The vapor pressure, or volatility, of compounds containing these groups often falls rapidly with increasing molecular size. Many of these compounds are produced from decaying matter or biological excretions while some are byproducts of microorganisms. For example, the compounds that produce body odor are the result of bacteria present in an individual's perspiration and not the perspiration itself.

Presently there are three common approaches to reduce unpleasant odors. The most common is to apply a fragrance that overpowers and masks the original odor. The competing scent is usually dispensed in the air where the odor is detected. In some cases, the unpleasant odor is replaced with a fragrance that is more acceptable. U.S. Pat. No. 8,192,723 discloses this type of composition. In other circumstances, the fragrance combines with the odor to produce a new undesirable odor. Unfortunately, because this approach does not neutralize the odor, it often returns.

Many of these deodorizing compositions are adapted for mist or aerosol dispensing. However, conventional spray ingredients include compounds that can affect an individual's health. These compounds include cocoamidopropyl betaine (a contact dermatitis agent), formaldehyde (a protein denaturant, skin sensitizer and probable carcinogen), morpholinium (an eye irritant and skin sensitizer), adamantane (a neurotransinission contact blocker, systemic sensitizer and possible reactant with RNA), benzalkonium chloride (a skin sensitizer), triethylene glycol (a neuromuscular depressor), and quaternary ammonium compounds (skin sensitizers). In spray form these compounds easily come into contact with skin, eyes and/or mucous membranes of the nasal cavity and/or respiratory tract were they are quickly absorbed into the blood. Consequently, they cannot be used in areas where individuals are present that may be compromised to chemical or microbiological challenges such as operating rooms, intensive care units or neonatal nurseries.

Another common approach reduces the vapor pressure of the odorous compound by altering pH. For example, under conditions of high pH, hydrogen sulfide, has almost no odor whereas under acidic conditions $H_2S$ gas is created. Ammonia is another example of the pH effect. Under acidic conditions the ammonia ion $NH_4^+$ is highly soluble in aqueous solution and produces little odor. However, when the pH of the solution is raised above 9, ammonia gas is rapidly volatilized. Therefore, adjusting the pH can reduce the concentration of the odorous compound in the gas phase by reducing its volatility. However, to be effective, all of the odor-producing compound must be reacted with the acid or base. Unfortunately, the amount or concentration of the odor-producing compound cannot be determined. Consequently, it is difficult to assure that the appropriate amount of acid or base will be applied to neutralize the odor-producing compound.

Other compositions chemically neutralize odors. U.S. Pat. No. 6,303,111 describes an odor-neutralizing composition comprising a transition metal complex such as disodium monocopper citrate or disodium monozinc citrate at a concentration range from 0.05% to 0.5%. While these compounds may be effective at neutralizing odors, their transition metal content raises medical concerns from continued use and exposure. Long-term exposure to copper can cause headaches, stomachaches, dizziness, vomiting and diarrhea. Zinc also has health concerns. Although humans can tolerate larger concentrations of zinc, too much of this metal can cause stomach cramps, skin irritations, vomiting, nausea and anemia. Very high levels of zinc can damage the pancreas, disturb protein metabolism, and cause arteriosclerosis.

U.S. Pat. No. 5,089,258 discloses a particulate composition comprising 0.1 to 30% by weight of citric acid and at least 50% weight of monovalent citric acid salt for removing strong offensive odors from clothing. However, a composition of citric acid and monovalent citric acid salts does not often remove the odor completely.

In some instances, a microorganism like bacteria is responsible for producing the odorous compound. Under this circumstance, a two-step approach is often used that first eliminates the microorganism followed by dispensing a fragrance to mask the existing odor. Most bacteria that produce unpleasant odorous compounds are anaerobic. Consequently, many treatments utilize hydrogen peroxide to produce oxygen that is highly toxic to anaerobic bacteria. Other antimicrobial agents include aryl 2-acetoxyethannoic acid (U.S. Pat. No. 5,874,071), hexachlorophene, bisphenol, quaternary ammonium compounds, bis-(2-pyridyl-1-oxide) disulfide (U.S. Pat. No. 2,742,476); molybdate derivatives (U.S. Pat. No. 3,027,371), stannous chloride derivative (U.S. Pat. No. 3,027,732) and stannous fluoride derivatives of bis-(2-pyridyl-1-oxide) disulfide (U.S. Pat. No. 3,346,578).

Other methods to eliminate bacteria include the use of drying compounds to reduce the moisture bacteria require for survival. Drying agents include aluminum chloride, aluminum chlorhydroxide, aluminum sulfate, aluminum potassium sulfate, aluminum phenolsulfonate, zinc oxide, zinc peroxide, zinc stearate and zinc phenolsulfonate.

Another method utilizes inhibitors of the bacteria or the bacterial enzyme responsible for the production of the odor causing compounds. U.S. Pat. No. 5,643,559 discloses a composition comprising zinc glycinate for inhibiting the bacterial exoenzymes that produce the steroidal axillary malodor. Unfortunately, the odor can return if, the bacteria are not completely eliminated; a sufficient amount of neutralizing reagent is not applied; or it is not adequately masked by a fragrance.

Therefore, there is a need in the field for a chemical formulation that does not merely, cover or mask the unpleasant odor with a fragrance; rely solely on acid/base neutralization of the odorous compound; or use chemicals that may cause health risks for consumers.

BRIEF SUMMARY OF THE INVENTION

The present invention is a composition and method of using the composition to reduce or eliminate odors on a surface. In one aspect of the present invention the composition is an aqueous solution of multivalent citrate salts. The method comprises the steps of applying this composition in sufficient volume to saturate the odorous surface and, after the composition has had time to react, absorbing the composition from the surface, thereby reducing or eliminating the odor.

In one embodiment, the composition is prepared from alkali metal citrate salts and may contain one or more of the alkali metals lithium, sodium, and/or potassium. These citrate salts may be divalent or trivalent or a combination of both and range in concentration from about 0.09M to about 0.90M. More specifically, in the concentration range of about 0.10M to about 0.50M.

In another embodiment, the composition further comprises a surfactant such as methanol, ethanol, propanol, isopropanol, primary butanol, secondary butanol and tertiary butanol. The concentration of the surfactant may range from about 0.9% to about 9.0% volume/volume and more specifically from about 2.0% to about 5.0% volume/volume.

In other embodiments, the composition may further comprise a natural or synthetic fragrance and/or coloring agent.

The composition and method of using the composition can reduce or eliminate odors resulting from smoke, decomposition, excrement, or biological excretion. This includes smoke (for example, from burning material such as wood, tobacco or *cannabis*), decomposing plant or animal matter, animal feces and urine, animal scent gland excretions like those released by skunks or cats and odors released from bacteria and fungi.

Another aspect of the present invention is the composition mixed with, or coated onto, an absorbent matrix such as clay or bentonite. Methods of preparing the absorbent matrix comprising multivalent citrate salts are also provided. One method comprises mixing a solid multivalent citrate salt composition into the absorbent matrix. Another method applies an aqueous solution of the composition to an absorbent granular matrix. The matrix is then dried and mixed to remove clumping.

In another aspect of the present invention a method is provided for reducing or eliminating body odors. This method comprises applying the composition as a solution, semi-solid or solid on an area of the body where the odor occurs, such as the underarm.

Other aspects of the invention are found throughout the specification.

BRIEF DESCRIPTION OF THE SEVERAL VIEWS OF THE DRAWINGS

None

DETAILED DESCRIPTION OF THE INVENTION

Unless defined otherwise, all terms used in this application have the same meaning as are commonly understood by one of skill in the art to which this invention belongs. All patents, patent applications and publications referred to herein, are incorporated by reference in their entirety. In the event that there is a plurality of definitions for a term, those in this section prevail.

The term "animal" as used herein refers to a living organism belonging to the kingdom Animalia including, for example, mammals, birds, reptiles and fishes.

The term "biological excretion" as used herein refers to fluids deposited by animals from their scent glands such as scents applied to objects by cats and dogs to mark their territory. This also includes fluids released from the anal sac of some animals as a defense mechanism to protect against predators such as the excretion sprayed by skunks. In addition, this term also refers to odorous compounds released by microorganisms such as bacteria and fungi.

The term "chelating agent" as used herein refers to a molecule or ion that is capable of forming multiple bonds to a metal or metal ion of a metalloenzyme. These molecules or ions may be organic or inorganic in composition and the metal may be a transition metal. This reaction, the complexing of or with the metal ion, often results in the interference with, or elimination of, the metalloenzyme's functionality. The chelation of other types of molecules, such as dimethyl telluride, can result in the sequestering of these molecules in solution, preventing them from entering the gaseous phase. In the case when these molecules are odor causing compounds, their odor can be eliminated, or reduced when they are prevented from entering the gaseous state.

The term "excrement" as used herein refers to odorous compounds associated with urine and feces of animals.

The phrase "for a time" as used herein refers to the time the composition remains on a treated surface before being removed, absorbed or dried. If the odor is not eliminated within the time selected, additional volumes of the chemical formulation may be applied until the odor is neutralized.

The term "fragrance" as used herein refers to a compound having a pleasant or pleasing odor that may be incorporated into the chemical formulation. Its purpose is not to cover or mask the odor, but to provide a scent that replaces or remains after the odor has been reduced or eliminated. The fragrance selected may be obtained from a natural source or synthetically prepared.

The term "multivalent citrate salt(s)" as used herein refers specifically to divalent (di-metallic) and trivalent (tri-metallic) citrate salt. The metal ions are preferably selected from the alkali metals specifically, lithium, sodium and potassium. The chemical formulation may comprise either or both divalent and trivalent citrate salts and may also comprise more than one of the alkali metal ions.

The term "saturated surface" as used herein refers to a treated surface having been contacted with a sufficient volume and concentration of the chemical formulation to effectively reduce or eliminate the odor. The amount of the formulation applied should be sufficient to completely infiltrate the area where the odor is detected. If the odor is not reduced or eliminated, additional volumes may be applied until the odor is neutralized.

The term "sufficient" as used herein refers to the amount of the chemical formulation applied to the effected area. If the odor is not reduced or eliminated by the initial application of the chemical formulation, additional volumes may be applied until the odor is neutralized. Consequently, the amount applied in a single treatment, or in multiple treatments, is sufficient when the odor is eliminated or reduced to a desired level.

The term "absorbent matrix" as used herein refers to a porous material that may retain multivalent citrate salts either through absorption of an aqueous solution of the chemical formulation or by mixing the absorbent matrix with a solid form of the chemical formulation. Absorbent matrixes that may be utilized with the present invention include clay, bentonite, alganite, zeolite, diatomite, sepiolite and sodium silicate.

In one aspect of the present invention, the composition is an aqueous solution comprising a multivalent citrate salt or a combination of multivalent citrate salts.

1. Multivalent Citrate Salt

In one embodiment, the composition is prepared from alkali metal citrate salts dissolved in water. These citrate salts may contain one or more of the alkali metal ions lithium, sodium, and/or potassium. Multivalent citrate salts may be obtained commercially from a variety of suppliers including, for example, Sigma-Aldrich (St. Louis, Mo., United States) or Fischer Scientific (Cambridge, United Kingdom). Unlike the alkali earth metal and transition metal citrate salts which have potential long-term exposure health concerns, no significant health effects have been reported from the use of multivalent alkali metal citrate salts for humans or domesticated animals.

Alkali metal citrate salts are readily soluble in water and can be prepared in a variety of concentrations for use in effectively reducing or eliminating odor. This is not the case with alkali earth metal and transition metal citrate salts, which are primarily insoluble in water. Consequently, these citrate salts may not able to be prepared in effective concentrations for reducing or eliminating odors.

Many compounds that cause offense odors have at least one functional group that can react with citrate salts. This reaction changes the structure of the compound, reducing or eliminating its odorous characteristics. Monovalent citrate salts are able to react with a single functional group, while multivalent citrate salts are able to react with two or three functional groups simultaneously. Consequently, chemical formulations comprising multivalent citrate salts are more efficient at neutralizing odors, requiring less volume and/or lower concentrations, than formulations prepared from monovalent citrate salts.

The multivalent citrate salts that comprise the chemical formulations of the present invention may be utilized independently or in combination. More specifically, the chemical formulation may comprise divalent citrate salts, trivalent citrate salts or a combination of divalent and trivalent citrate salts. In addition, the chemical formulations may comprise citrate salt(s) having a single type of alkali metal ion or combination of alkali metal ions. For example, a chemical formulation may comprise multivalent lithium citrate salts, multivalent sodium citrate salts, multivalent potassium salts, a combination of multivalent lithium and sodium citrate salts, a combination of multivalent sodium and potassium citrate salts, a combination of multivalent lithium and potassium citrate salts or a combination of multivalent lithium, sodium and potassium citrate salts.

The chemical formulation may be provided in a concentration range from about 0.09M to about 0.90M and more specifically from about 0.10M to about 0.50M. The pH range of these chemical formulations at concentrations between 0.09M to 0.90M is about 7.2 to about 8.3.

Solid and semisolid forms of the chemical formulations may also be prepared. As a solid, in either a granulated or powdered form, the chemical formulation is dispensed directly onto an effected area or may be mixed with an absorbent matrix for application to an effected area. Absorbent matrixes that may be utilized with the present invention include clay, bentonite, alganite, zeolite, diatomite, sepiolite and sodium silicate. These matrixes may be coated or mixed with the chemical formulation and used for absorbing a variety of aqueous odorous compounds including for example, cat urine.

A semisolid form of the chemical formulation may also be prepared by a variety of methods known to those skilled in the art for making stick deodorants. For example, U.S. Pat. No. 7,128,901 discloses a process for forming a freestanding deodorant solid stick.

2. Surfactant

Citrate salts are hydrophilic and dissolve relatively easily in water. However, the functional groups of the odorous compounds often make them moderately hydrophobic and less water-soluble. Because of this incompatibility, a surfactant may be used to increase the solubility of the odorous compounds in aqueous solution, allowing them to chemically react more easily with the multivalent citrate salts. The reaction neutralizes these compounds making them less volatile.

A number of surfactants may be utilized with the present invention. Preferably the surfactant is an alcohol such as for example methanol, ethanol, propanol, isopropanol, primary butanol, secondary butanol and tertiary butanol. These alcohols may be purchased from a number of commercial suppliers including Sigma-Aldrich (St. Louis, Mo.) and Fischer Scientific (Cambridge, United Kingdom). The concentration of the surfactant ranges from about 0.9% to about 9.0% volume/volume and more specifically from about 2.0% to about 5.0% volume/volume.

3. Chelating Agents

In one mode of action, chelating agents are capable of forming multiple bonds with a metal ion. In other words, a chelating agent is a multidentate ligand that is a Brønsted-Lowry base. Chelating agents are able to react with Brønsted-Lowry acid functional groups in organic molecules or ions such as thiols and/or carboxylates. When chelation occurs, one or more of the bonds maintaining the metal atom or ion within the metalloenzyme are dismantled and the functionality of the enzyme dependent upon the presence of the metal ion is reduced or eliminated. In one particular enzyme of interest, urease, the decomposition of urine into ammonia is reduced or eliminated.

In another mode of action, chelating agents are capable of forming multiple bonds with other molecules maintaining them in in a particular chemical state, such as for example, the complexing of dimethyl telluride which forces this compound to remain in solution phase preventing it from becoming a gas and thereby its detection when in the gaseous phase.

A number of chelating agents may be utilized with the present invention to enhance the application of a solution of multivalent citrate salts of the present invention. Preferably the chelating agent added to the multivalent citrate salt solution is ethylenediaminetetraacetic acid (EDTA) or its enantiomers and mono-valence, bi-valence, tri-valence or tetra-valence salts, sodium tripolyphosphate or disodium pyrophosphate. The concentration of these chelating agents can range from approximately 0.9 to 9.0% volume/volume and more particularly from approximately 2.0% to 5.0% volume/volume.

3. Fragrance and/or Coloring Agent

In other embodiments, the composition may further comprise a fragrance and/or color. The fragrance is not provided to cover or mask the odor, but is a scent that replaces or remains after the odor has been reduced or eliminated. A variety of natural or synthetic fragrances may be used. Fragrances may be obtained from a variety of suppliers including Wellington Fragrance Company (Livonia, Mich. United States) or Ultra International Limited (New Delhi, India).

In some circumstances, it may be desirable to color the chemical formulation to make it more attractive to consumers. A variety of coloring agents both natural and synthetic may be utilized in the chemical formulation. Selection of the color will depend on specific desirable characteristics. Of particular interest is selecting a color that will not stain or discolor the surface on which the chemical formulation is applied. Coloring agents may be obtained from a variety of suppliers for example, CPSColor (Vantaa, Finland).

4. Methods of Use

The method of reducing or eliminating odors comprises the steps of applying the chemical formulations of the present invention in sufficient volume to saturate the surface and, after the composition has had time to react, removing or absorbing the composition from the surface.

A variety of surfaces may be treated with the methods and compositions of the present invention. Surfaces include for example textiles (such as clothing, carpets, drapes, fabric furniture and the like), hard surfaces (such as walls and floors including those prepared from cement, wood, bamboo, stone, sheet-rock, metals or synthetic materials such as linoleum, Pergo™ (Pergo AG, Baar, Switzerland)), flexible surfaces (such as plastics or polymers) and painted surfaces.

A variety of odors can be reduced or eliminated with the compositions and methods of the present invention. Some examples include odors associated with animal excrement (such as urine and feces), smoke (resulting from fire or burning of tobacco or *cannabis*), animal excretions (such as the anal sac excretion of skunks or the scent gland excretions of a cat), decaying plant or animal material and odors from microorganisms (such as those from bacteria and fungi).

A variety of chemical formulations comprising alkali metal multivalent citrate salts may be prepared and utilized to reduce or eliminate odors. Table 1 shows a basic aqueous composition of the chemical formulation comprising a trisodium citrate salt and methanol as the surfactant.

TABLE 1

A basic composition comprising a single multivalent citrate salt and a surfactant

| Chemical Component | Concentration (% by weight) |
| --- | --- |
| Trisodium Citrate | 8.7 |
| Methanol | 1.6 |
| Water | 89.7 |

Table 2 shows an aqueous composition comprising a mixture of trivalent and divalent citrate salts having the same alkali metal counter ions with isopropanol as a surfactant.

TABLE 2

A composition comprising two different multivalent citrate salts having the same alkali metal ion

| Chemical Component | Concentration (% by weight) |
| --- | --- |
| Trisodium Citrate | 5.8 |
| Disodium Citrate | 2.7 |
| isopropanol | 1.5 |
| Water | 90.0 |

Table 3 shows an aqueous composition comprising a mixture of trivalent and divalent citrate salts having different alkali metals counter ions with tertiary butanol as a surfactant.

TABLE 3

A composition comprising a combination of two multivalent citrate salts having different alkali metal ions

| Chemical Component | Concentration (% by weight) |
| --- | --- |
| Trisodium Citrate | 5.8 |
| Dipotassium Citrate | 3.0 |
| tertiary butanol | 1.5 |
| Water | 89.7 |

The compositions may further include a fragrance. The fragrance component is not employed to mask odors but is a pleasant scent to replace the odor neutralized by the alkali metal citrate salts.

Table 4 shows an aqueous composition comprising a mixture of trivalent and divalent citrate salts having different alkali metal counter ions, tertiary butanol as a surfactant and a fragrance.

TABLE 4

A composition comprising a combination of two multivalent citrate salts having different alkali metal ions and a fragrance

| Chemical Component | Concentration (% by weight) |
| --- | --- |
| Trisodium Citrate | 5.8 |
| Dipotassium Citrate | 3.0 |
| ethanol | 1.6 |
| Lemon | 0.001-0.01 |
| Water | 89.6 |

Table 5 shows a basic aqueous composition of the chemical formulation comprising a trisodium citrate salt, methanol as the surfactant and a chelating agent.

TABLE 5

A basic composition comprising a single multivalent citrate salt, a surfactant and chelating agent

| Chemical Component | Concentration (% by weight) |
| --- | --- |
| Trisodium Citrate | 8.7 |
| Methanol | 1.6 |
| Tetrasodium Ethylenediaminetetraacetate | 0.5 |
| Water | 89.2 |

Table 6 shows an aqueous composition comprising a mixture of trivalent and divalent citrate salts having the same alkali metal counter ions with isopropanol as a surfactant and a chelating agent.

TABLE 6

A composition comprising two different multivalent citrate salts having the same alkali metal ion and chelating agent

| Chemical Component | Concentration (% by weight) |
| --- | --- |
| Trisodium Citrate | 5.8 |
| Disodium Citrate | 2.7 |
| isopropanol | 1.5 |
| Tetrasodium Ethylenediaminetetraacetate | 1.6 |
| Water | 88.4 |

Table 7 shows an aqueous composition comprising a mixture of trivalent and divalent citrate salts having different alkali metals counter ions with tertiary butanol as a surfactant and a chelating agent.

TABLE 7

A composition comprising a combination of two multivalent citrate salts having different alkali metal ions and chelating agent

| Chemical Component | Concentration (% by weight) |
| --- | --- |
| Trisodium Citrate | 5.8 |
| Dipotassium Citrate | 3.0 |
| tertiary butanol | 1.5 |
| Sodium tripolyphosphate | 2.8 |
| Water | 86.9 |

The compositions of the present invention are particularly adapted for pouring directly onto a surface or spray dispensing. Once formulated the compositions are passed through a suitable sterilizing filter system, such as a Stericup Filter unit (EMD Millipore, Billerica, Mass.) or a Pall Filtration sterile filtration system (Pall Corporation, Port Washington, N.Y.), to remove potentially harmful microorganisms. The composition may be packaged in bottles or aerosol containers with a self-pressurized aerosol spray dispensing system. Any propellant known in the art may be used in such aerosol containers. Preferably, the propellant will comprise carbon dioxide or nitrogen, which provides smaller particle size spray droplets. Suitable pressures range from about 50 to about 60 psi, although other pressures may be employed.

Alternatively, the filtered composition may be packaged in a container having a pump-type spray dispenser. In this type of system, the formulation will further comprise a preservative that prevents microbial growth because the dispensed composition is replaced by ambient air. In another alternate embodiment, the compositions may be employed in an electrical spray dispenser, for example in operating rooms, intensive care units and other health care facilities. Additional spray dispensers known in the art may also be used in combination with the chemical formulations of the present invention.

In another aspect of the invention, the spray may be applied to an absorbent matrix such as clay or bentonite. Once the formulation is absorbed into the matrix it is dried and mixed to remove clumping. When a solution containing an odorous compound comes in contact with the matrix the citrate salts are activated and the compound is neutralized reducing or eliminating the odor. Alternatively, a dry formulation of the multivalent citrate salts may be mixed with the absorbent matrix so that the matrix is coated with the multivalent citrate salts or salts are evenly distributed within the matrix. This type of matrix can be particularly useful as cat litter to eliminate the odor associated with urine. Table 8 shows a dry composition comprising a mixture of trivalent and divalent citrate salts having different alkali metal counter ions.

TABLE 8

| Dry composition | |
|---|---|
| Chemical Component | Concentration (% by weight) |
| Trisodium Citrate | 5.8 |
| Dipotassium Citrate | 3.0 |
| Water | 91.2 |

Table 9 shows a basic aqueous composition of the chemical formulation comprising a trisodium citrate salt and methanol as the surfactant and a chelating agent.

TABLE 9

| A basic dry composition comprising a single multivalent citrate salt, a surfactant and chelating agent | |
|---|---|
| Chemical Component | Concentration (% by weight) |
| Trisodium Citrate | 5.8 |
| Dipotassium Citrate | 3.0 |
| Disodium pyrophosphate | 1.6 |
| Water for distribution prior to evaporation so there is a dry product on a surface such as cat litter | 89.6 |

The information set forth above is provided to give those of ordinary skill in the art a complete disclosure and description of how to make and use the embodiments of the device and methods, and are not intended to limit the scope of what the inventor regards as his invention. Modifications of the above-described modes (for carrying out the invention that are obvious to persons of skill in the art) are intended to be within the scope of the following claims. All publications, patents, and patent applications cited in this specification are incorporated herein by reference.

The invention claimed is:

1. A method for reducing or eliminating odors on a surface, said method comprising:
applying an aqueous solution containing multi-valent alkali metal citrate salt, wherein said multi-valent citrate salt is trisodium citrate salt, wherein the concentration of said trisodium citrate salt in said aqueous solution is about 0.3M and a surfactant, wherein said surfactant is ethanol, wherein said percentage of ethanol is 1.0% v/v, wherein said trisodium citrate salt in said aqueous solution reacts with odorous compounds on said surface for a time and in a volume sufficient to absorb or adsorb into said surface, thereby reducing or eliminating said odors from said surface.

2. The method according to claim 1, further comprising the step of drying or allowing to dry said aqueous solution from said treated surface after said time.

3. The method according to claim 1, wherein said aqueous solution further comprises a chelating agent, wherein said chelating agent is ethylenediaminetetraacetic acid (EDTA) or its enantiomers or salts, wherein the concentration of said chelating agent is from about 0.9 to about 9.0% volume/volume or from about 2.0% to about 5.0% volume/volume.

4. The method according to claim 1, wherein said odors are the result of excrement from a human, an animal or bacteria.

5. The method according to claim 4, wherein said excrement is feces or urine.

* * * * *

UNITED STATES PATENT AND TRADEMARK OFFICE
CERTIFICATE OF CORRECTION

| | |
|---|---|
| PATENT NO. | : 11,154,474 B2 |
| APPLICATION NO. | : 16/280112 |
| DATED | : October 26, 2021 |
| INVENTOR(S) | : Manus B. Monroe |

It is certified that error appears in the above-identified patent and that said Letters Patent is hereby corrected as shown below:

In the Specification

Column 1, Lines 8-11, replace "This patent application is a continuation-in-part application of patent application Ser. No. 14/758,399 filed 29 Jun. 2015 and claims the benefit of the filing date of PCT/US2013/29787 filed 8 Mar. 2013 under 35 U.S.C. §371." with -- This application is a continuation-in-part of patent application Serial No. 14/758,399 filed 24 August 2015, now abandoned, and claims the benefit of the filing date of PCT/US2013/29787 filed 8 March 2013 under 35 U.S.C. §371.--

Signed and Sealed this
Fifteenth Day of November, 2022

Katherine Kelly Vidal
*Director of the United States Patent and Trademark Office*